United States Patent [19]

Hunsucker et al.

[11] 4,105,552
[45] Aug. 8, 1978

[54] METHOD OF CONTROLLING THE GROWTH OF MICROORGANISMS

[75] Inventors: Jerry Hoyt Hunsucker; James R. Selleck, Jr., both of Terre Haute, Ind.

[73] Assignee: IMC Chemical Group, Inc., Terre Haute, Ind.

[21] Appl. No.: 796,942

[22] Filed: May 16, 1977

[51] Int. Cl.² ............................................. C02B 3/06
[52] U.S. Cl. ........................................ 210/64; 424/325
[58] Field of Search ............ 71/67; 162/161; 210/64; 260/584 R; 424/325, 343

[56] References Cited

U.S. PATENT DOCUMENTS

| | | | |
|---|---|---|---|
| 2,383,564 | 8/1945 | Ralston et al. | 424/325 |
| 3,117,850 | 1/1964 | Skaptason | 260/584 R |
| 3,432,603 | 3/1969 | Zenitz | 424/325 |
| 3,874,869 | 4/1975 | Koppensteiner et al. | 210/64 |
| 3,954,873 | 5/1976 | Gipson | 424/325 |

*Primary Examiner*—Thomas G. Wyse
*Attorney, Agent, or Firm*—Robert H. Dewey; Howard E. Post

[57] ABSTRACT

A method of controlling the growth of microorganisms by applying to them or to the environment inhabited by them a compound represented by the formula

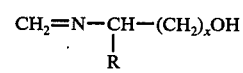

where R can be hydrogen, methyl or ethyl and $x$ is 1 or 2.

5 Claims, No Drawings

METHOD OF CONTROLLING THE GROWTH OF MICROORGANISMS

BACKGROUND OF THE INVENTION

This invention relates to a composition of antimicrobial agents. In a particular aspect this invention relates to an antimicrobial composition useful for controlling the growth of microorganisms.

One of the problems in metalworking industries is the susceptibility of metalworking fluids (which are emulsions of oil or chemical lubricants in water) to microbial attack. Were it not for this microbial contamination, the oil could be used for many months, but actually the microbial growth shortens the working life of the oil considerably. Microbial action may cause the emulsion to break and become acidic, thus causing corrosion problems. Some of the microbes may be pathogenic which can cause skin infections and other industrial health problems. In addition the microbial mycelia can clog pumps and valves, and often a foul odor develops. In a large installation, frequent replacement of metalworking fluids is costly.

SUMMARY OF THE INVENTION

It is an object of this invention to provide an antimicrobial composition.

It is another object of this invention to provide an antimicrobial composition having particular utility in aqueous systems.

Other objects will be apparent to those skilled in the art from the description herein.

It is the discovery of this invention to provide a method of controlling the growth of microorganisms by applying to them or to the environment inhabited by them a compound represented by the formula:

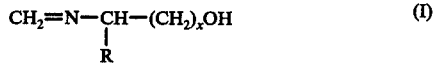  (I)

where R can be hydrogen, methyl or ethyl and $x$ is 1 or 2.

DETAILED DESCRIPTION

The compounds of the present invention are effective for controlling the growth of a wide variety of microorganisms. They are generally effective to combat the growth of microorganisms at a concentration of at least about 500 ppm. However, depending on the vigor of the organisms, the length of time during which growth should be suppressed, etc., concentrations of about 1000 ppm or even up to 1500 or 2000 ppm may be preferred.

These compounds are readily prepared by reacting formaldehyde with the corresponding alkanolamine represented by the formula

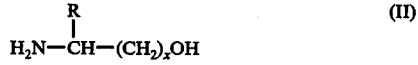  (II)

where R and $x$ have the same meanings defined above. The reaction proceeds at room temperature with evolution of heat, but additional heating, e.g. up to about 100°–110° C, is required to bring the reaction to completion. The product can be used without further purification or it can be refined. The lower boiling compounds, e.g. where R is hydrogen or methyl, can be purified by distillation at reduced pressure, but the higher boiling compounds are preferably purified by recrystallization from a suitable solvent, e.g. water, or a lower aliphatic alcohol.

The method of controlling the growth of microorganisms of this invention comprises application of an antimicrobial compound represented by the above formula I to a substratum infested with the microorganisms to be controlled or to a substratum to be protected from infestation with the microorganisms. The term substratum as used herein is intended to mean the environment or medium upon which an organism grows and includes both animate and inanimate matter, such as animal and vegetable, living or dead, and the soil. The terms microbe and microorganism as used herein are intended to include bacteria and fungi. The term antimicrobial as used herein is intended to include the terms bactericidal, bacteriostatic, fungicidal and fungistatic. No attempt has been made to determine if the products actually cause the death of the organism or merely prevent their growth. The compounds are especially useful in cutting oils for metalworking, latex paints, and recirculated cooling water.

The compounds of this invention are water-soluble, at least to the extent that they are effective antimicrobials. Preferably they are supplied to the microorganisms or to the environment inhabited by them as an aqueous solution. However they are also very soluble in organic solvents such as aliphatic alcohols and ketones and can be employed as a non-aqueous solution if desired. Also, if preferred, the compounds can be used as such without dilution.

In controlling the growth of microorganisms the combination of this invention is supplied to the organisms or to their environment in a lethal or toxic amount. This can be done by dispersing a compound or mixture thereof, or a composition containing it, in, on or over an environment or substratum infested with, or to be protected from, the microorganisms. A compound of this invention or a mixture containing it can be dispersed in any conventional method which permits contact between the organisms and the antimicrobial agents of this invention. The system to be protected may contain a compound of this invention added by the manufacturer at the time of manufacture or preparation. Alternatively, the proper amount of the compound can be added ad libitum.

The invention will be better understood with reference to the following examples. It is understood that the examples are intended to be illustrative only and it is not intended that the invention be limited thereby.

EXAMPLE 1

Monoethanolamine 61 g (1 mole) and paraformaldehyde 33 g (1 mole) were mixed in a reaction vessel and heated with stirring for 1 hour at 60° C. The reaction vessel was then connected to a distillation column and heated under reduced pressure of 7 mm and 60° C to distill the product. There was obtained N-methyleneaminoethanol, neutral equivalent 75.4, calculated 73.094.

The antimicrobial properties of N-methyleneaminoethanol were determined by the tube dilution method. Media for the bacterial cultures was trypticase soya broth at pH 7.3 prepared as known in the art, and the media for the fungi was Sabouraud broth at pH 5.6, also prepared as known in the art. The inoculum was standardized by the pour plate method for a total viable organism count. The amount of the inoculum per tube was 5 ml at a population of $10^5$ organisms per ml.

The compound was tested for anti-bacterial and anti-fungal activity against nine bacteria (4 Gram positive and 5 Gram negative) and eight fungi (6 molds and 2 yeasts). The results are listed in the table. They are reported as minimum inhibitory concentration, which is the range between the highest concentration which permits growth and the lowest concentration which prevents growth. They increase exponentially. Because of uncontrollable variables, such as the vigor of the organism, the data are reproducible to about plus or minus one range.

| MINIMUM INHIBITORY CONCENTRATIONS | |
|---|---|
| Organism | |
| BACTERIA | |
| Bacillus subtilis | 250–500 ppm |
| Staphylococcus aureus | 250–500 |
| Streptococcus faecalis | 250–500 |
| Sarcina lutea | 125–250 |
| Escherichia coli | 250–500 |
| Aerobacter aerogenes | 125–250 |
| Pseudomonas aeruginosa | 250–500 |
| Salmonella typhii | 250–500 |
| Desulfovibrio aestaurii | 125–250 |
| FUNGI | |
| Cladosporium herbarum | 250–500 |
| Cephalosporium species | 65–125 |
| Trichophyton mentagrophytes | 33–65 |
| Aspergillus niger | 500–1000 |
| Aureobasidium pullulans | 500–1000 |
| Fusarium moniliforme | 125–250 |
| Saccharomyces cerevisiae | 65–125 |
| Candida albicans | 1000–2000 |

A cutting oil emulsion is prepared according to the following formula:

| Light mineral oil | 20 parts |
|---|---|
| Water | 76.9 |
| N-Methyleneaminoethanol | 0.1 |
| Emulsifying agent | 3 |
| | 100 |

The emulsion remains free from microbial contamination for a long period of time when used as a cutting oil.

EXAMPLE 2

The experiment of example 1 is repeated in all essential details except that 1-amino-3-propanol is substituted for monoethanolamine on an equimolar basis. There is obtained N-methylene-3-amino-1-propanol. It is tested for antimicrobial activity and is found to be effective against a wide spectrum of bacteria and fungi. When incorporated in metalworking fluids, at 500–1000 ppm or more, it controls the growth of microorganisms for a prolonged period.

EXAMPLE 3

The experiment of example 1 is repeated in all essential details except that 2-amino-1-propanol is substituted for monoethanolamine on an equimolar basis. There is obtained N-methylene-2-amino-1-propanol. It is tested for antimicrobial activity and is found to be effective against a wide spectrum of bacteria and fungi. When incorporated in metalworking fluids, at 500–1000 ppm or more, it controls the growth of microorganisms for a prolonged period.

EXAMPLE 4

The experiment of example 1 is repeated in all essential details except that 2-amino-1-butanol is substituted for monoethanolamine on an equimolar basis. There is obtained N-methylene-2-amino-1-butanol. It is tested for antimicrobial activity and is found to be effective against a wide spectrum of bacteria and fungi. When incorporated in metalworking fluids, at 500–1000 ppm or more, it controls the growth of microorganisms for a prolonged period.

We claim:

1. A method of controlling the growth of microorganisms by applying to them or to the environment inhabited by them a compound represented by the formula

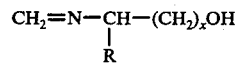

where R can be hydrogen, methyl or ethyl and $x$ is 1 or 2.

2. A compound of claim 1 wherein R is hydrogen and $x$ is 1.

3. A compound of claim 1 wherein R is hydrogen and $x$ is 2.

4. A compound of claim 1 wherein R is methyl and $x$ is 1.

5. A compound of claim 1 wherein R is ethyl and $x$ is 1.

* * * * *